United States Patent
Musil

(10) Patent No.: US 9,079,873 B2
(45) Date of Patent: Jul. 14, 2015

(54) PROCESS FOR THE PREPARATION OF BENZYL [(3AS,4R,6S,6AR)-6-HYDROXY-2,2-DIMETHYLTETRAHYDRO-3AH-CYCLO-PENTA[D][1,3]DIOXOL]-4-YL]CARBAMATE AND INTERMEDIATES IN THE PROCESS

(75) Inventor: Tibor Musil, Cheshire (GB)

(73) Assignee: AstraZeneca AB, Sodertalje (SE)

( * ) Notice: Subject to any disclaimer, the term of this patent is extended or adjusted under 35 U.S.C. 154(b) by 41 days.

(21) Appl. No.: 14/117,077

(22) PCT Filed: May 11, 2012

(86) PCT No.: PCT/SE2012/050498
§ 371 (c)(1),
(2), (4) Date: Jan. 29, 2014

(87) PCT Pub. No.: WO2012/158099
PCT Pub. Date: Nov. 22, 2012

(65) Prior Publication Data
US 2014/0135509 A1 May 15, 2014

Related U.S. Application Data

(60) Provisional application No. 61/540,084, filed on Sep. 28, 2011, provisional application No. 61/485,691, filed on May 13, 2011.

(51) Int. Cl.
*C07D 317/44* (2006.01)
*C07B 53/00* (2006.01)

(52) U.S. Cl.
CPC .............. *C07D 317/44* (2013.01); *C07B 53/00* (2013.01)

(58) Field of Classification Search
CPC .................................................... C07D 317/44
See application file for complete search history.

(56) References Cited

FOREIGN PATENT DOCUMENTS

| WO | 00/34283 | 6/2000 |
|----|----------|--------|
| WO | 01/92263 | 12/2001 |
| WO | WO 0192263 A1 * | 12/2001 |
| WO | 2009/064249 | 5/2009 |

OTHER PUBLICATIONS

Sigma Aldrich. "Chiral Resolving Reagents." (c) Nov. 2, 2010. Available from: < http://web.archive.org/web/20101102192922/http://www.sigmaaldrich.com/chemistry/chemistry-products.html?TablePage=16265015 >.*
Vanderbilt University. "Protecting Groups." (c) Jun. 2010. Available from: < http://web.archive.org/web/20100601210500/http://www.vanderbilt.edu/AnS/Chemistry/Rizzo/chem223/protect.pdf >.*
Ranganathan et al., "2-Aza-3-Oxabicyclo[2.2.1]heptene Hydrochloride: An Exceptionally Versatile Synthon for Carbocyclic Sugars and Nucleosides," Tetrahedron (1997) 53(9):3347-3362.
Shireman et al., "Rapid syntheses of either enantiomer of important carbocyclic nucleoside precursors," Tetrahedron Letters (2000) 41:9537-9540.
Rajappan et al., "A Protected Form of (1S,2R,3S,4R)-4-Aminocyclopentane-1,2,3-Triol, a Useful Precursor to 5'-Nor Carbocyclic Nucleosides," Synthetic Communications, (2001) 31(18), 2849-2854.

* cited by examiner

*Primary Examiner* — Noble Jarrell
*Assistant Examiner* — John S Kenyon
(74) *Attorney, Agent, or Firm* — Pepper Hamilton LLP

(57) ABSTRACT

The present invention is directed to a process for the preparation of benzyl [(3aS,4R,6S,6aR)-6-hydroxy-2,2-dimethyltetrahydro-3aH-cyclopenta[d][1,3]dioxol-4-yl]carbamate (VI),

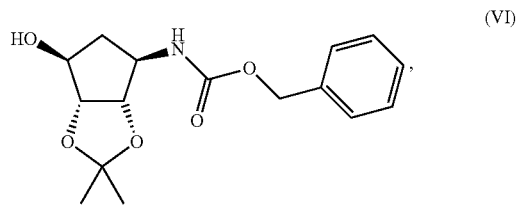

(VI)

to products of said process and the use thereof.

2 Claims, No Drawings

PROCESS FOR THE PREPARATION OF BENZYL [(3AS,4R,6S,6AR)-6-HYDROXY-2,2-DIMETHYLTETRAHYDRO-3AH-CYCLOPENTA[D][1,3]DIOXOL]-4-YL]CARBAMATE AND INTERMEDIATES IN THE PROCESS

FIELD OF THE INVENTION

The present invention is directed to a process for the preparation of benzyl [(3aS,4R,6S,6aR)-6-hydroxy-2,2-dimethyltetrahydro-3aH-cyclopenta[d][1,3]dioxol-4-yl]carbamate (VI),

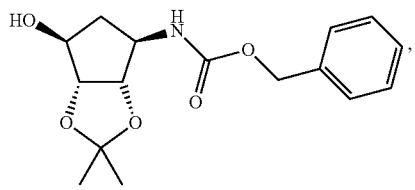

an intermediate useful in the synthesis of pharmaceuticals, for example Ticagrelor, to products of said process and the use thereof.

BACKGROUND

The synthesis of compounds (II) and (III) are described in *Tetrahedron* 1997, 53, 3347.

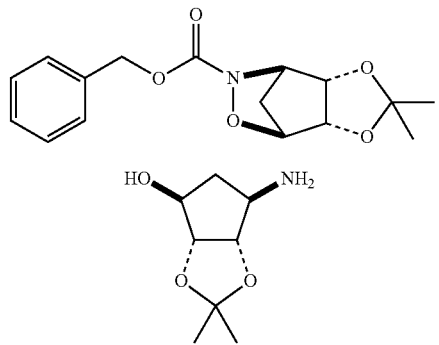

The syntheses of either the free amine or the hydrochloride salt of compound (IV) are described in WO99/05142, *Tetrahedron Lett.*, 2000, 41, 9537 and *Synth. Commun.* 2001, 31, 2849. The synthesis of a diastereomerically pure dibenzoyl-L-tartrate salt of compound (IV) is described in WO 2009/064249.

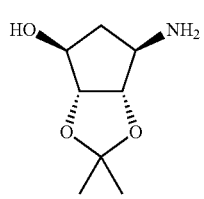

The synthesis of benzyl [(3aS,4R,6S,6aR)-6-hydroxy-2,2-dimethyltetrahydro-3aH-cyclopenta[d][1,3]dioxol-4-yl]carbamate (VI) is described in WO00/34283 and WO 01/92263.

DESCRIPTION OF THE INVENTION

The present invention is directed to a process for the preparation of benzyl [(3aS,4R,6S,6aR)-6-hydroxy-2,2-dimethyltetrahydro-3aH-cyclopenta[d][1,3]dioxol-4-yl]carbamate (VI),

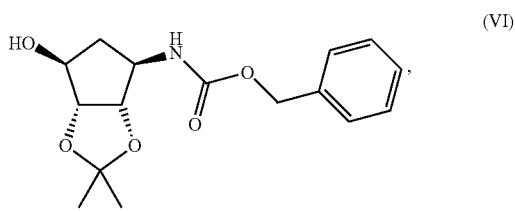

comprising the steps of
(a) mixing a compound of formula (III),

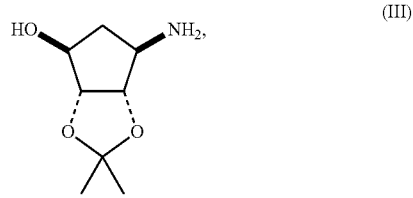

with an enantiomerically pure protected amino acid to form a diastereoisomeric salt,
(b) crystallizing said salt to deliver a protected amino acid salt of a compound of formula (IV),

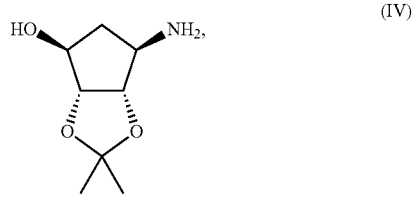

(c) treating the protected amino acid salt of the compound of formula (IV) with an acid, and
(d) reacting the product from c) with benzyl chloroformate in the presence of a suitable base, such as potassium carbonate.

The process according to the present invention is particularly useful for large-scale production of benzyl [(3aS,4R,6S,6aR)-6-hydroxy-2,2-dimethyltetrahydro-3aH-cyclopenta[d][1,3]dioxol-4-yl]carbamate (VI) by providing for example higher yields, less amounts of chemicals used in the process (or excluded), better volume capacity, shorter manufacturing time, more robust process with the possibility of recovery of the chiral protected amino acid as well as solvents used in the resolution.

The process for preparation of benzyl [(3aS,4R,6S,6aR)-6-hydroxy-2,2-dimethyltetrahydro-3aH-cyclopenta[d][1,3]dioxol-4-yl]carbamate (VI) may start from a compound of formula (III), which may be prepared by procedures known in the art. The compound of formula (III) is then resolved by crystallization of a diastereomerically pure salt using an enantiomerically pure protected amino acid to give the corresponding diastereomerically pure protected amino acid salt of the compound of formula (IV). The amino acid salt of the compound of formula (IV) is first treated with an acid and subsequently reacted with benzyl chloroformate in the presence of a suitable base, such as potassium carbonate, to deliver (VI).

Alternatively, the process for preparation of benzyl [(3aS,4R,6S,6aR)-6-hydroxy-2,2-dimethyltetrahydro-3aH-cyclopenta[d][1,3]dioxol-4-yl]carbamate (VI) may start from a compound of formula (I), which may be prepared by procedures known in the art or as described in the Examples. Compound (I) is converted to compound (III) as known in the art or as described in the Examples. Subsequently, the compound of formula (III) is resolved by crystallization of a diastereomerically pure protected amino acid salt using an enantiomerically pure protected amino acid to give the corresponding diastereomerically pure salt of the compound of formula (IV). The amino acid salt of the compound of formula (IV) is then treated with an acid and subsequently reacted with benzyl chloroformate in the presence of a suitable base, such as potassium carbonate, to deliver (VI).

The following scheme illustrates the process for preparation of benzyl [(3aS,4R,6S,6aR)-6-hydroxy-2,2-dimethyltetrahydro-3aH-cyclopenta[d][1,3]dioxol-4-yl]carbamate (VI) via (3aS,4R,6S,6aR)-6-hydroxy-2,2-dimethyltetrahydro-3aH-cyclopenta[d][1,3]dioxol-4-aminium (2S)-2-[(tert-butoxycarbonyl)amino]-3-phenylpropanoate (Va) or via (3aS,4R,6S,6aR)-6-hydroxy-2,2-dimethyltetrahydro-3aH-cyclopenta[d][1,3]dioxol-4-aminium (2S)-2-[(tert-butoxycarbonyl)amino]-4-methylpentanoate (Vb):

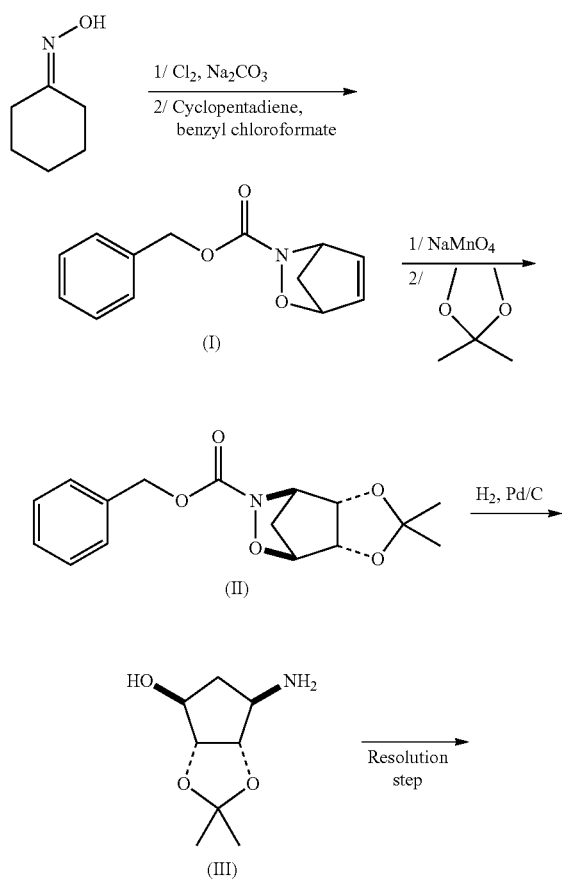

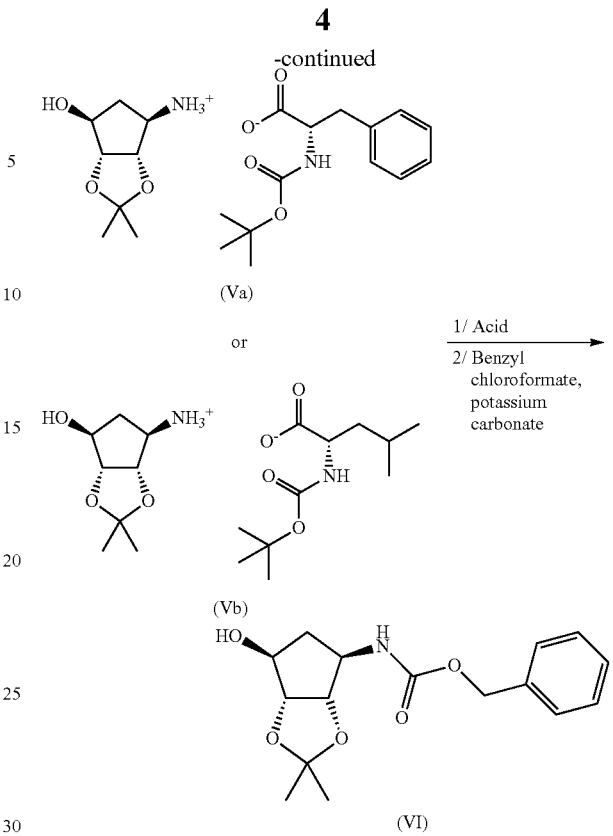

One embodiment of the present invention is a process for the preparation of a protected amino acid of the compound of formula (IV). A further embodiment of the present invention is the 1:1-salt between a protected amino acid and the compound of formula (IV). Still a further embodiment of the present invention is the 1:1-salt between L-Boc-phenylalanine and the compound of formula (IV). Said salt can also be named N-(tert-butoxycarbonyl)-L-phenylalanine-(3aR,4S,6R,6aS)-6-amino-2,2-dimethyltetrahydro-3aH-cyclopenta[d][1,3]dioxol-4-ol (1:1) or (3aS,4R,6S,6aR)-6-hydroxy-2,2-dimethyltetrahydro-3aH-cyclopenta[d][1,3]dioxol-4-aminium (2S)-2-[(tert-butoxycarbonyl)amino]-3-phenylpropanoate (Va). Still a further embodiment of the present invention is the 1:1 salt between L-Boc-leucine and the compound of formula (IV). Said salt can also be named N-(tert-butoxycarbonyl)-L-leucine-(3aR,4S,6R,6aS)-6-amino-2,2-dimethyltetrahydro-3aH-cyclopenta[d][1,3]dioxol-4-ol (1:1) or (3aS,4R,6S,6aR)-6-hydroxy-2,2-dimethyltetrahydro-3aH-cyclopenta[d][1,3]dioxol-4-aminium (2S)-2-[(tert-butoxycarbonyl)amino]-4-methylpentanoate (Vb).

In one embodiment of the invention, the protecting group for the enantiomerically pure protected amino acids is selected from Boc, Cbz or Bz. In a further embodiment of the invention, the enantiomerically pure protected amino acids suitable for use in the resolution step is selected from L-Boc-phenylalanine, L-Boc-leucine, Cbz-L-alanine, Bz-L-alanine, Cbz-L-phenylalanine, Boc-L-alanine, Cbz-L-tyrosine or Boc-L-tyrosine. In a further embodiment of the invention, the enantiomerically pure protected amino acid is selected from the opposite (D) enantiomers. In still a further embodiment of the invention, the enantiomerically pure protected amino acid is L-Boc-phenylalanine. In still a further embodiment of the invention, the enantiomerically pure protected amino acid is L-Boc-leucine.

In one embodiment of the invention, solvents useful for the resolution step giving a diastereomerically pure salt of a compound of formula (IV) may be selected from aliphatic alcohols (such as methanol, ethanol, n-propanol, iso-propanol, n-butanol, iso-butanol or tert-butanol), aliphatic esters (such as ethyl acetate, butyl acetate or iso-propyl acetate), aliphatic ketones (such as acetone, methyl ethyl ketone (MEK) or methyl iso-butyl ketone (MIBK)), aromatic solvents (such as toluene or xylene) and mixtures thereof. In a further embodiment of the present invention, the solvent in step (a) is selected from aliphatic alcohols, aromatic solvents and mixtures thereof. In still a further embodiment of the present invention, the solvent in step (a) is a mixture of iso-propanol and an aromatic solvent. In still a further embodiment of the present invention, the solvent in step (a) is a mixture of iso-propanol and toluene. In still a further embodiment of the present invention, the solvent in step (a) is iso-propanol. In still a further embodiment of the present invention, the solvent in step (a) is a mixture of an aliphatic ketone and an aromatic solvent. In still a further embodiment of the present invention, the solvent in step (a) is a mixture of MIBK and an aromatic solvent. In still a further embodiment of the present invention, the solvent in step (a) is MIBK. In still a further embodiment of the present invention, the solvent in step (a) is a mixture of methyl ethyl ketone and an aromatic solvent. In still a further embodiment of the present invention, the solvent in step (a) is MEK.

In one embodiment of the invention, the resolution with the enantiomerically pure protected amino acid is performed with 0.55 to 1.4 equivalents of enantiomerically pure protected amino acid to compound (III). In a further embodiment of the present invention, the resolution with the enantiomerically pure protected amino acid is performed with 0.5 to 0.8 equivalents of enantiomerically pure protected amino acid to compound (III). In still a further embodiment of the present invention, the resolution with the enantiomerically pure protected amino acid is performed with 0.55 equivalents of enantiomerically pure protected amino acid to compound (III).

In one embodiment of the invention, the acid in step c) is selected from sulfuric acid, hydrochloric acid, hydrobromic acid, phosphoric acid, sodium hydrogen sulfate, sodium dihydrogenphosphate or an organic acid such as oxalic acid, malic acid, maleic acid or citric acid. In a further embodiment of the present invention, the acid in step c) is hydrochloric acid or oxalic acid.

In one embodiment of the invention, there is provided a protected amino acid salt of a compound of formula (IV),

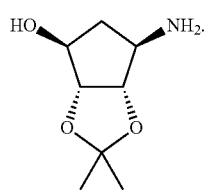

(IV)

In one embodiment of the invention, there is provided the compound (3aS,4R,6S,6aR)-6-hydroxy-2,2-dimethyltetrahydro-3aH-cyclopenta[d][1,3]dioxol-4-aminium (2S)-2-[(tert-butoxycarbonyl)amino]-3-phenylpropanoate (Va),

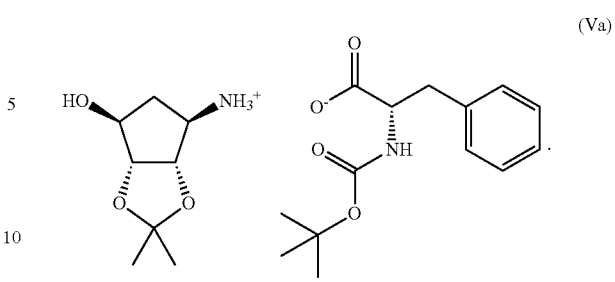

(Va)

In a further embodiment of the invention, there is provided the compound (3aS,4R,6S,6aR)-6-hydroxy-2,2-dimethyltetrahydro-3aH-cyclopenta[d][1,3]dioxol-4-aminium (2S)-2-[(tert-butoxycarbonyl)amino]-4-methylpentanoate (Vb),

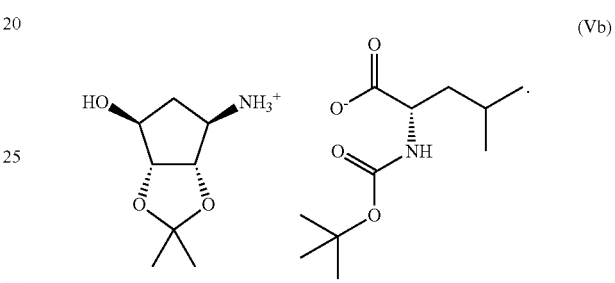

(Vb)

In one embodiment of invention, the resolution step giving a diastereomerically pure salt of a compound of formula (IV) is initially performed at temperatures from 0° C. to the boiling point of the solvent to fully dissolve the components or the formed diastereoisomeric salts. When the components have been dissolved, in one embodiment of invention, the temperature of the solution is adjusted to a temperature of from −50° C. to +50° C., to obtain a crystalline salt of the compound (IV). In a further embodiment of invention, when the components have been dissolved, the temperature of the solution is adjusted to a temperature of from −20° C. to 20° C., to obtain a crystalline salt of the compound (IV). The salt may thereafter be recrystallized from a solvent similar or different to the one used above to improve the optical and chemical purity.

A further embodiment of the present invention is the use of the protected amino acid salt of the compound of formula (IV) in the preparation of Ticagrelor, {1S-[1α, 2α, 3β (1S*,2R*), 5β]}-3-(7-{[2-(3,4-difluorophenyl)cyclopropyl]amino}-5-(propylthio)-3H-1,2,3-triazolo[4,5-d]pyrimidin-3-yl)-5-(2-hydroxyethoxy)cyclopentane-1,2-diol.

The term "diastereomerically pure salt" is defined as a salt between an enantiomerically pure cation (such as monocation of amine (IV) in the present invention) and an enantiomerically pure anion (protected amino acid monoanion in the present invention).

ABBREVIATIONS

Boc tert-butoxycarbonyl
Bz benzoyl
Cbz carboxybenzyl
MEK methyl ethyl ketone
MIBK methyl iso-butyl ketone

EXAMPLES

Example 1

Benzyl 2-oxa-3-azabicyclo[2.2.1]hept-5-ene-3-carboxylate (I)

Cyclohexanone oxime (20.04 g, 171.8 mmol) and methyl t-butyl ether (110 mL) were added to a reactor at 25° C. and stirred under $N_2$ (g). The solution was cooled to −10° C. and $Cl_2$ (g) was added during 15 min until a deep blue, clear solution was obtained. Vacuum was applied to remove remaining $Cl_2$ and possible HCl from the reaction mixture. The temperature was set to −2° C., and a solution of $Na_2CO_3$ (11.03 g, 103 mmol) in water (90 mL) was slowly added during 30 min. The phases were separated and the organic phase transferred to a solution of $Na_2CO_3$ (19.3 g, 180.3 mmol) in water (126 mL) at 15° C. Benzyl chloroformate (32.3 g, 179.87 mmol) was added and the reaction mixture stirred for 10 min after which cyclopentadiene (25.2 g, 362.16 mmol) was added and the reaction mixture stirred for 3 h. Vacuum was applied and the remaining cyclopentadiene was removed. The phases were separated and the organic phase containing the title product was taken further directly to Example 2 as below.

Example 2

Benzyl 5,6-dihydroxy-2-oxa-3-azabicyclo[2.2.1] heptane-3-carboxylate (II)

The organic phase from Example 1 was added to iso-propanol (24 mL) and (water 62 mL). Sodium permanganate (10% (aq), 215.8 mL) was slowly added via syringe during 4 h at 25° C. $SO_2$ (36.13 g) was added during 25 min. The beige slurry was filtered, the filter washed with methyl t-butyl ether, after which the phases were separated and the aqueous phase extracted with methyl t-butyl ether. Sodium chloride was added to the aqueous phase which was further extracted with toluene. The combined organic phases were evaporated to deliver the title compound.

Benzyl 5,6-dihydroxy-2-oxa-3-azabicyclo[2.2.1]heptane-3-carboxylate was transformed into (3aR,4S,6R,6aS)-6-amino-2,2-dimethyltetrahydro-3aH-cyclopenta[d][1,3]dioxol-4-ol (III) utilizing processes as described in *Tetrahedron*, 1997, 53, 3347.

Example 3

(3aS,4R,6S,6aR)-6-Hydroxy-2,2-dimethyltetrahydro-3aH-cyclopenta[d][1,3]dioxol-4-aminium (2S)-2-[(tert-butoxycarbonyl)amino]-3-phenylpropanoate (Va)

N-(tert-Butoxycarbonyl)-L-phenylalanine (4.1 g, 99%, 15.2 mmol), (3aR,4S,6R,6aS)-6-amino-2,2-dimethyltetrahydro-3aH-cyclopenta[d][1,3]dioxol-4-ol (2.6 g, 96%, 14.5 mmol), toluene (1.5 mL) and iso-propanol (19.5 mL) were taken to a flask with a stirrer. The mixture was heated under stirring to 63° C. when a clear solution was obtained. The solution was cooled and crystallization started at 53° C. The slurry was further cooled to 0° C. and stirred at this temperature for 60 min. The crystals were isolated on a glass filter, washed with cooled iso-propanol (17.5 mL) and dried in vacuum at 40° C. to give an amount of 2.73 g. The assay by titration was 99.7% and ee by LC 98.8%. The yield was 42.7%.

Example 4

(3aS,4R,6S,6aR)-6-Hydroxy-2,2-dimethyltetrahydro-3aH-cyclopenta[d][1,3]dioxol-4-aminium (2S)-2-[(tert-butoxycarbonyl)amino]-3-phenylpropanoate (Va), alternative procedure (3aR,4S,6R,6aS)-6-Amino-2,2-dimethyltetrahydro-3aH-cyclopenta[d][1,3]dioxol-4-ol (80.0 g, 96%, 443.4 mmol), toluene (46.9 mL) and iso-propanol (500 mL) were taken to a flask with a stirrer. The mixture was heated, with stirring, to 31° C. when N-(tert-butoxycarbonyl)-L-phenylalanine (124.8 g, 99%, 465.5 mmol) was added together with iso-propanol (99 mL). The mixture was further heated to 66° C. when a clear solution was obtained. The solution was cooled and crystallization started at 55° C. The slurry was further cooled to ambient temperature and stirred overnight. The next day the slurry was cooled to 0° C. and stirred at this temperature for 120 min. The crystals were isolated on a glass filter, washed with cooled iso-propanol (500 mL) and dried in vacuum at 40° C. to give an amount of 85.8 g. The assay by titration was 99.0% and ee by LC 99.2%. The yield was 43.3%.

Example 5

(3aS,4R,6S,6aR)-6-Hydroxy-2,2-dimethyltetrahydro-3aH-cyclopenta[d][1,3]dioxol-4-aminium (2S)-2-[(tert-butoxycarbonyl)amino]-3-phenylpropanoate (Va), alternative procedure N-(tert-Butoxycarbonyl)-L-phenylalanine iso-propanol solution (10.0 g, 23%, 8.7 mmol) recycled from a iso-propanol solution containing ca. 14% w/w of a mixture of (3aR,4S,6R,6aS)-6-hydroxy-2,2-dimethyltetrahydro-3aH-cyclopenta[d][1,3]dioxol-4-aminium (2S)-2-[(tert-butoxycarbonyl)amino]-3-phenylpropanoate and (3aS,4R,6S,6aR)-6-hydroxy-2,2-dimethyltetrahydro-3aH-cyclopenta[d][1,3]dioxol-4-aminium (2S)-2-[(tert-butoxycarbonyl)amino]-3-phenylpropanoate in a ratio of 9:1 and ca. 1% w/w of N-(tert-butoxycarbonyl)-L-phenylalanine, (3aR,4S,6R,6aS)-6-amino-2,2-dimethyltetrahydro-3aH-cyclopenta[d][1,3]dioxol-4-ol (1.5 g, 96%, 8.3 mmol), toluene (0.9 mL, 8.3 mmol) and iso-propanol (1.6 mL) were mixed in a small flask and heated under stirring. At 67° C. a clear solution was obtained. The solution was cooled to 50° C. when crystallization occurred. The slurry was further cooled to ambient temperature and stirred overnight. The next day the slurry was cooled to 0° C. and stirred for 120 min. The crystals were isolated on a glass filter, washed with cooled iso-propanol (12 mL) and dried in vacuum at 40° C. to give an amount of 1.59 g. The assay by titration was 99.1% and ee by LC 99.0%. The yield was 43.3%.

Example 6

(3aS,4R,6S,6aR)-6-Hydroxy-2,2-dimethyltetrahydro-3aH-cyclopenta[d][1,3]dioxol-4-aminium (2S)-2-[(tert-butoxycarbonyl)amino]-3-phenylpropanoate (Va), alternative procedure with 0.85 equivalents N-(tert-butoxycarbonyl)-L-phenylalanine (3aR,4S,6R,6aS)-6-Amino-2,2-dimethyltetrahydro-3aH-cyclopenta[d][1,3]dioxol-4-ol (5.21 g, 96%, 28.9 mmol), N-(tert-butoxycarbonyl)-L-phenylalanine (6.58 g, 24.54 mmol) toluene (1 mL) and iso-propanol (27.5 mL) were taken to a flask with a stirrer. The mixture was heated, with stirring, to 68° C. when a clear solution was obtained. The solution was cooled and crystallization started at 53° C. The slurry was further cooled to ambient temperature and stirred overnight. The next day the slurry was cooled to 0° C. and stirred at this temperature for 90 min. The crystals were isolated on a glass filter, washed with iso-propanol (3×5 mL) and dried in vacuum at 40° C. to give an amount of 5.8 g (45.5%, 98.8% ee).

Example 7

(3aS,4R,6S,6aR)-6-Hydroxy-2,2-dimethyltetrahydro-3aH-cyclopenta[d][1,3]dioxol-4-aminium (2S)-2-[(tert-butoxycarbonyl)amino]-3-phenylpropanoate (Va), alternative procedure with 0.7 equivalents N-(tert-butoxycarbonyl)-L-phenylalanine (3aR,4S,6R,6aS)-6-Amino-2,2-dimethyltetrahydro-3aH-cyclopenta[d][1,3]dioxol-4-ol (5.21 g, 96%, 28.9 mmol), N-(tert-butoxycarbonyl)-L-phenylalanine (5.42 g, 20.21 mmol), toluene (1 mL) and iso-propanol (25 mL) were taken to a flask with a stirrer. The mixture was heated, with stirring, to 70° C. when a clear solution was obtained. The solution was cooled and crystallization started at 56° C. The slurry was further cooled to ambient temperature and stirred 50 min. The slurry was cooled to 0° C. and stirred at this temperature for 80 min. The crystals were isolated on a glass filter, washed with iso-propanol (4×5 mL) and dried in vacuum at 40° C. to give an amount of 5.48 g (44.6%, 99.6% ee).

Example 8

(3aS,4R,6S,6aR)-6-Hydroxy-2,2-dimethyltetrahydro-3aH-cyclopenta[d][1,3]dioxol-4-aminium (2S)-2-[(tert-butoxycarbonyl)amino]-3-phenylpropanoate (Va), alternative procedure with 0.6 equivalents N-(tert-butoxycarbonyl)-L-phenylalanine (3aR,4S,6R,6aS)-6-Amino-2,2-dimethyltetrahydro-3aH-cyclopenta[d][1,3]dioxol-4-ol (5.00 g, 27.71 mmol), N-(tert-butoxycarbonyl)-L-phenylalanine (4.46 g, 16.63 mmol), toluene (2.93 mL) and MIBK (37.44 mL) were taken to a flask with a stirrer. The mixture was heated, with stirring, to 89° C. when a clear solution was obtained. The solution was cooled and crystallization started at 75° C. The slurry was stirred for 1 h at 72° C. after which it was slowly cooled during 3 h to ambient temperature. The slurry was cooled to 0° C. and stirred at this temperature for 90 min. The crystals were isolated on a glass filter, washed with MIBK (2×10 mL) and dried in vacuum at 40° C. to give an amount of 5.55 g (45.3%, 98.4% ee).

Example 9

(3aS,4R,6S,6aR)-6-Hydroxy-2,2-dimethyltetrahydro-3aH-cyclopenta[d][1,3]dioxol-4-aminium (2S)-2-[(tert-butoxycarbonyl)amino]-3-phenylpropanoate (Va), alternative procedure with 0.85 equivalents N-(tert-butoxycarbonyl)-L-phenylalanine (3aR,4S,6R,6aS)-6-Amino-2,2-dimethyltetrahydro-3aH-cyclopenta[d][1,3]dioxol-4-ol (5.00 g, 27.71 mmol), N-(tert-butoxycarbonyl)-L-phenylalanine (6.31 g, 23.55 mmol), toluene (2.93 mL) and MIBK (37.44 mL) were taken to a flask with a stirrer. The mixture was heated, with stirring, to 89° C. when a clear solution was obtained. The solution was cooled and crystallization started at 75° C. The slurry was stirred for 1 h at 72° C. after which it was slowly cooled during 3.5 h to ambient temperature. The slurry was cooled to 0° C. and stirred at this temperature for 90 min. The crystals were isolated on a glass filter, washed with MIBK (2×10 mL) and dried in vacuum at 40° C. to give an amount of 5.79 g (47.3%, 98.6% ee).

Example 10

(3aS,4R,6S,6aR)-6-Hydroxy-2,2-dimethyltetrahydro-3aH-cyclopenta[d][1,3]dioxol-4-aminium (2S)-2-[(tert-butoxycarbonyl)amino]-3-phenylpropanoate (Va), alternative procedure with 1.05 equivalents N-(tert-butoxycarbonyl)-L-phenylalanine (3aR,4S,6R,6aS)-6-Amino-2,2-dimethyltetrahydro-3aH-cyclopenta[d][1,3]dioxol-4-ol (2.50 g, 13.86 mmol), N-(tert-butoxycarbonyl)-L-phenylalanine (3.91 g, 14.59 mmol), toluene (1.47 mL) and MIBK (18.7 mL) were taken to a flask with a stirrer. The mixture was heated, with stirring, to 84° C. The slurry was cooled to 75° C. The slurry was stirred for 30 min at 75° C. after which it was slowly cooled over night to ambient temperature. The slurry was cooled to 0° C. and stirred at this temperature for 130 min. The crystals were isolated on a glass filter, washed with MIBK (2×5 mL) and dried in vacuum at 40° C. to give an amount of 2.91 g (47.1%, 97.2% ee).

Example 11

(3aS,4R,6S,6aR)-6-hydroxy-2,2-dimethyltetrahydro-3aH-cyclopenta[d][1,3]dioxol-4-aminium (2S)-2-[(tert-butoxycarbonyl)amino]-4-methylpentanoate (Vb), procedure with 0.6 equivalents N-(tert-butoxycarbonyl)-L-leucine (3aR,4S,6R,6aS)-6-Amino-2,2-dimethyltetrahydro-3aH-cyclopenta[d][1,3]dioxol-4-ol (5.00 g, 27.71 mmol), N-(tert-butoxycarbonyl)-L-leucine (3.88 g, 16.63 mmol), toluene (2.93 mL) and iso-propanol (37.44 mL) were taken to a flask with a stirrer. The mixture was heated, with stirring, to 79° C. The solution was cooled and crystallization started at 73° C. The slurry was further cooled during 3.5 h to ambient temperature. The slurry was cooled to 0° C. and stirred at this temperature for 120 min. The crystals were isolated on a glass filter, washed with iso-propanol (2×10 mL) and dried in vacuum at 40° C. to give an amount of 5.09 g (45.4%, 99.2% ee).

Example 12

(3aS,4R,6S,6aR)-6-hydroxy-2,2-dimethyltetrahydro-3aH-cyclopenta[d][1,3]dioxol-4-aminium (2S)-2-[(tert-butoxycarbonyl)amino]-4-methylpentanoate (Vb), procedure with 0.85 equivalents N-(tert-butoxycarbonyl)-L-leucine (3aR,4S,6R,6aS)-6-Amino-2,2-dimethyltetrahydro-3aH-cyclopenta[d][1,3]dioxol-4-ol (5.00 g, 27.71 mmol), N-(tert-butoxycarbonyl)-L-leucine (5.50 g, 23.55 mmol), toluene (2.93 mL) and iso-propanol (37.44 mL) were taken to a flask with a stirrer. The mixture was heated, with stirring, to 79° C. The cloudy solution was cooled during 4.5 h to ambient temperature. The slurry was cooled to 0° C. and stirred at this temperature for 120 min. The crystals were isolated on a glass filter, washed with iso-propanol (2×10 mL) and dried in vacuum at 40° C. to give an amount of 5.24 g (46.7%, 99.4% ee).

Example 13

(3aS,4R,6S,6aR)-6-hydroxy-2,2-dimethyltetrahydro-3aH-cyclopenta[d][1,3]dioxol-4-aminium (2S)-2-[(tert-butoxycarbonyl)amino]-4-methylpentanoate (Vb), alternative procedure with 0.60 equivalents N-(tert-butoxycarbonyl)-L-leucine (3aR,4S,6R,6aS)-6-Amino-2,2-dimethyltetrahydro-3aH-cyclopenta[d][1,3]dioxol-4-ol (5.00 g, 27.71 mmol), N-(tert-butoxycarbonyl)-L-leucine (3.88 g, 16.61 mmol), toluene (2.93 mL) and MIBK (37.4 mL) were taken to a flask with a stirrer. The mixture was heated, with stirring, to 93° C. The cloudy solution was cooled during 3.5 h to ambient temperature and stirred over night. The slurry was cooled to 0° C. and stirred at this temperature for 75 min. The crystals were isolated on a glass filter, washed with MIBK (2×10 mL) and dried in vacuum at 40° C. to give an amount of 5.39 g (47.2%, 96.2% ee).

Example 14

(3aS,4R,6S,6aR)-6-hydroxy-2,2-dimethyltetrahydro-3aH-cyclopenta[d][1,3]dioxol-4-aminium (2S)-2-[(tert-butoxycarbonyl)amino]-4-methylpentanoate (Vb), alternative procedure with 0.85 equivalents N-(tert-butoxycarbonyl)-L-leucine (3aR,4S,6R,6aS)-6-Amino-2,2-dimethyltetrahydro-3aH-cyclopenta[d][1,3]dioxol-4-ol (5.00 g, 27.71 mmol), N-(tert-butoxycarbonyl)-L-leucine (5.50 g, 23.54 mmol), toluene (2.93 mL) and MIBK (37.4 mL) were taken to a flask with a stirrer. The mixture was heated, with stirring, to 93° C. The cloudy solution was cooled during 3.5 h to ambient temperature and stirred over night. The slurry was cooled to 0° C. and stirred at this temperature for 85 min. The crystals were isolated on a glass filter, washed with MIBK (2×10 mL) and dried in vacuum at 40° C. to give an amount of 5.61 g (48.8%, 94.8% ee).

Example 15

(3aS,4R,6S,6aR)-6-hydroxy-2,2-dimethyltetrahydro-3aH-cyclopenta[d][1,3]dioxol-4-aminium (2S)-2-[(tert-butoxycarbonyl)amino]-4-methylpentanoate (Vb), alternative procedure with 1.05 equivalents N-(tert-butoxycarbonyl)-L-leucine (3aR,4S,6R,6aS)-6-Amino-2,2-dimethyltetrahydro-3aH-cyclopenta[d][1,3]dioxol-4-ol (2.50 g, 13.86 mmol), N-(tert-butoxycarbonyl)-L-leucine (3.40 g, 14.55 mmol), toluene (1.47 mL) and MIBK (18.72 mL) were taken to a flask with a stirrer. The mixture was heated, with stirring, to 91° C. The slurry was cooled during 2 h to ambient temperature and stirred over night. The slurry was cooled to 0° C. and stirred at this temperature for 120 min. The crystals were isolated on a glass filter, washed with MIBK (2×5 mL) and dried in vacuum at 40° C. to give an amount of 2.77 g (48.5%, 96.4% ee).

Example 16

(3aS,4R,6S,6aR)-6-hydroxy-2,2-dimethyltetrahydro-3aH-cyclopenta[d][1,3]dioxol-4-aminium (2S)-2-[(tert-butoxycarbonyl)amino]-4-methylpentanoate (Vb), alternative procedure with 0.85 equivalents N-(tert-butoxycarbonyl)-L-leucine in MEK (3aR,4S,6R,6aS)-6-Amino-2,2-dimethyltetrahydro-3aH-cyclopenta[d][1,3]dioxol-4-ol (3.00 g, 16.63 mmol), toluene (1.76 mL) and MEK (22.46 mL) were taken to a flask with a stirrer. The mixture was heated, with stirring, to 40° C. and N-(tert-butoxycarbonyl)-L-leucine (3.30 g, 14.13 mmol) was added. The cloudy solution heated to 78° C. after which it was was cooled during 2.5 h to ambient temperature. The slurry was cooled to 0° C. and stirred over night. The crystals were isolated on a glass filter, washed with MEK (2×10+1×5 mL) and dried in vacuum at 40° C. to give an amount of 3.32 g (48.1%, 96.2% ee).

Example 17

Benzyl [(3aS,4R,6S,6aR)-6-hydroxy-2,2-dimethyltetrahydro-3aH-cyclopenta[d][1,3]dioxol-4-yl] carbamate (VI)

To (3aS,4R,6S,6aR)-6-hydroxy-2,2-dimethyltetrahydro-3aH-cyclopenta[d][1,3]dioxol-4-aminium (2S)-2-[(tert-butoxycarbonyl)amino]-3-phenylpropanoate (10.06 g, 22.32 mmol) was added 30 mL ethyl acetate. The resulting thick slurry was put on ice-bath and stirred for 80 min. HCl (1 M, 24.5 mL, 24.5 mmol) was slowly added during 25 min while the temperature was kept below 5° C. (pH aqueous phase: 1-2). The phases were separated and the organic phase was washed with 10 mL of water after which the aqueous phases were combined. Potassium carbonate (10.3 g, 73.78 mmol) was dissolved in 25 mL of water. MIBK (30 mL) and benzyl chloroformate (4.17 g, 23.22 mmol) were added at 20° C. The combined aqueous phases were added slowly over 15 min and the mixture was warmed at 30° C. for 25 min without stirring. The phases were separated and the organic phase washed with 10 mL water. The organic phase was evaporated until about 11 g was remaining. Water (40 mL) was added and evaporation was continued until about 25 g was remaining. The mixture was filtered and the isolated product was washed with iso-octane and then dried at 40° C. in vacuum oven overnight. After drying, the title product was isolated (6.54 g), HPLC-purity: 97.7% (area), $^1$H-NMR assay: 100%.

From the original organic phase, 4.54 g N-(tert-butoxycarbonyl)-L-phenylalanine was recovered.

The invention claimed is:
1. (3aS,4R,6S,6aR)-6-hydroxy-2,2-dimethyltetrahydro-3aH-cyclopenta[d][1,3]dioxol-4-aminium (2S)-2-[(tert-butoxycarbonyl)amino]-3-phenylpropanoate (Va),

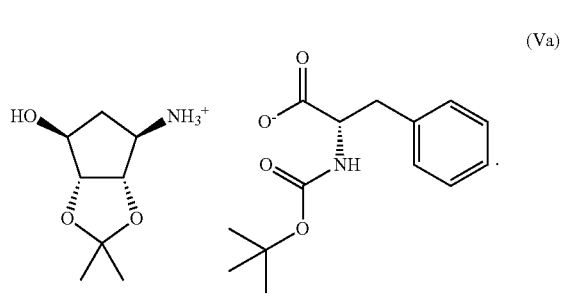 [SMILES: CC1(C)O[C@@H]2[C@H](O1)[C@@H](O)C[C@H]2[NH3+] ; CC(C)(C)OC(=O)N[C@@H](Cc1ccccc1)C(=O)[O-]]

2. (3aS,4R,6S,6aR)-6-hydroxy-2,2-dimethyltetrahydro-3aH-cyclopenta[d][1,3]dioxol-4-aminium (2S)-2-[(tert-butoxycarbonyl)amino]-4-methylpentanoate (Vb),
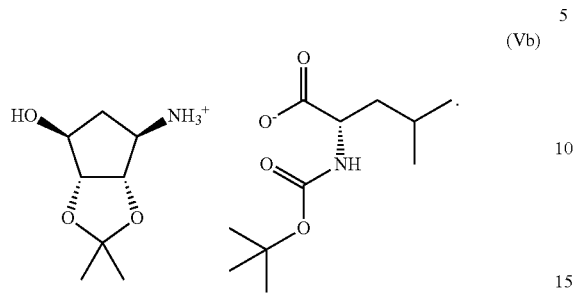
(Vb)
* * * * *